(12) United States Patent
Kim et al.

(10) Patent No.: US 11,629,116 B2
(45) Date of Patent: Apr. 18, 2023

(54) PLASTICIZER COMPOSITION AND RESIN COMPOSITION INCLUDING THE SAME

(71) Applicant: LG CHEM, LTD., Seoul (KR)

(72) Inventors: Hyun Kyu Kim, Daejeon (KR); Seok Ho Jeong, Daejeon (KR); Woo Hyuk Choi, Daejeon (KR); Yun Ki Cho, Daejeon (KR); Jeong Ju Moon, Daejeon (KR); Joo Ho Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 17/051,373

(22) PCT Filed: May 30, 2019

(86) PCT No.: PCT/KR2019/006517
§ 371 (c)(1),
(2) Date: Oct. 28, 2020

(87) PCT Pub. No.: WO2019/240409
PCT Pub. Date: Dec. 19, 2019

(65) Prior Publication Data
US 2021/0230098 A1    Jul. 29, 2021

(30) Foreign Application Priority Data

Jun. 12, 2018 (KR) .................. 10-2018-0067654
May 29, 2019 (KR) .................. 10-2019-0063107

(51) Int. Cl.
| | | |
|---|---|---|
| *C07C 69/75* | (2006.01) | |
| *C07C 69/704* | (2006.01) | |
| *C08K 5/101* | (2006.01) | |
| *C08K 5/12* | (2006.01) | |

(52) U.S. Cl.
CPC ............ *C07C 69/75* (2013.01); *C07C 69/704* (2013.01); *C08K 5/101* (2013.01); *C08K 5/12* (2013.01)

(58) Field of Classification Search
CPC ..................................................... C07C 69/75
See application file for complete search history.

(56) References Cited

U.S. PATENT DOCUMENTS

| | | | |
|---|---|---|---|
| 10,072,133 B2 | 9/2018 | Wagner et al. | |
| 10,287,415 B2 | 5/2019 | Pfeiffer et al. | |
| 10,329,402 B2 | 6/2019 | Pfeiffer et al. | |
| 2007/0287781 A1 | 12/2007 | Grass et al. | |
| 2013/0066000 A1* | 3/2013 | Freese ................ | C08K 5/0016 524/285 |
| 2016/0326346 A1* | 11/2016 | Gourdin ................ | C08K 5/101 |
| 2016/0326347 A1 | 11/2016 | Wagner et al. | |
| 2017/0081501 A1 | 3/2017 | Kim et al. | |
| 2017/0181929 A1 | 6/2017 | Ichikawa et al. | |
| 2017/0313848 A1 | 11/2017 | Pfeiffer et al. | |
| 2017/0313850 A1 | 11/2017 | Pfeiffer et al. | |
| 2018/0163018 A1 | 6/2018 | Kim et al. | |
| 2018/0171103 A1 | 6/2018 | Kim et al. | |
| 2018/0282512 A1 | 10/2018 | Kim et al. | |
| 2018/0291178 A1 | 10/2018 | Kim et al. | |
| 2018/0319953 A1 | 11/2018 | Kim et al. | |
| 2021/0115028 A1 | 4/2021 | Kim et al. | |

FOREIGN PATENT DOCUMENTS

| | | |
|---|---|---|
| CN | 100999601 | 7/2007 |
| CN | 101085736 A | 12/2007 |
| CN | 102040815 A | 5/2011 |
| CN | 103965564 A | 8/2014 |
| CN | 104191770 | 12/2014 |
| CN | 105899585 A | 8/2016 |
| CN | 106102688 A | 11/2016 |
| CN | 106351039 A * | 1/2017 |
| CN | 106795324 A | 5/2017 |
| CN | 106795325 A | 5/2017 |
| CN | 107075218 A | 8/2017 |
| CN | 107108958 A | 8/2017 |
| EP | 3211029 A1 | 8/2017 |
| EP | 3342811 A1 | 7/2018 |
| EP | 3805303 A1 | 4/2021 |
| JP | 2012-166483 | 9/2012 |
| JP | 2015-193817 | 11/2015 |
| KR | 10-0957134 | 5/2010 |
| KR | 10-2016-0047221 | 5/2016 |
| KR | 10-2016-0105830 | 9/2016 |

(Continued)

OTHER PUBLICATIONS

English machine translation of Zheng (CN 106351039) (Year: 2017).*
Fiume et al. (Int. J. Toxicol. 2014, 33 (supplement 2), 16S-46S) (Year: 2014).*

(Continued)

*Primary Examiner* — Michael F Pepitone
(74) *Attorney, Agent, or Firm* — Dentons US LLP

(57) ABSTRACT

Provided is a plasticizer composition including: a cyclohexane-1,2-diester-based substance of the following Chemical Formula 1; and a citrate-based substance of the following Chemical Formula 2:

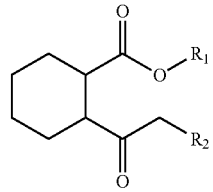

Chemical Formula 1

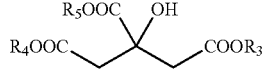

Chemical Formula 2 wherein in Chemical Formula 1 and Chemical Formula 2:
$R_1$ and $R_2$ each independently are a C8 to C10 alkyl group; and
$R_3$ to $R_5$ each independently are a C5 to C10 alkyl group.

10 Claims, No Drawings

(56) References Cited

FOREIGN PATENT DOCUMENTS

| | | |
|---|---|---|
| KR | 10-2016-0106657 | 9/2016 |
| KR | 10-2017-0066547 | 6/2017 |
| KR | 10-2017-0066548 | 6/2017 |
| KR | 10-2017-0121060 | 11/2017 |
| KR | 10-2017-0141599 | 12/2017 |
| TW | 201815930 A | 5/2018 |
| TW | 201819503 A | 6/2018 |
| WO | 2015104309 A1 | 7/2015 |
| WO | 2016055573 A1 | 4/2016 |
| WO | 2017-183877 A1 | 10/2017 |
| WO | 2018-008914 A1 | 1/2018 |
| WO | 2019-240405 A1 | 12/2019 |

OTHER PUBLICATIONS

Database WPI Week 202006, Dec. 19, 2019, Thomson Scientific, London, GB; AN 2019-A6173K, XP002803286 (3 Pages).
Database WPI Week 201808, Thomson Scientific, London, GB; AN 2018-02946G, XP002803288 (3 Pages).
Long Zhang et al. "Synthesis and Application of a New Environmental Friendly Plasticize", American Journal of Biomedical Science and Engineering, vol. 1, No. 1, Dec. 31, 2015, pp. 9-19 (11 Pages).
Ruyin Wang et al., "Morphology, Mechanical Properties, and Durability of Poly(Lactic Acid) Plasticized With Di(Isononyl) Cyclohexane-1,2-Dicarboxylate", Polymer Engineering and Science, Dec. 31, 2009, pp. 2414-2420 (7 Pages).

* cited by examiner

PLASTICIZER COMPOSITION AND RESIN COMPOSITION INCLUDING THE SAME

CROSS-REFERENCE TO RELATED APPLICATIONS

This application is a National Stage Application of International Application No. PCT/KR2019/006517 filed on May 30, 2019, which claims priority to and the benefit of Korean Patent Application No. 10-2018-0067654, filed on Jun. 12, 2018, and Korean Patent Application No. 10-2019-0063107, filed on May 29, 2019, the disclosures of which are incorporated herein by reference in their entirety.

TECHNICAL FIELD

The present invention relates to a plasticizer composition and a resin composition including the same, and more particularly, to a plasticizer composition that is environmentally friendly and has high stability and excellent basic properties and a resin composition including the same.

BACKGROUND

Conventionally, a plasticizer forms an ester through a reaction between an alcohol and a polycarboxylic acid such as phthalic acid or adipic acid. In addition, in consideration of domestic and international regulations for phthalate-based plasticizers harmful to humans, there is ongoing research on plasticizer compositions that can replace phthalate-based plasticizers such as terephthalate-, adipate-, and other polymer-based plasticizers.

In the polyvinyl chloride (PVC) compound industry requiring high heat resistance and low volatile loss as main desired physical properties, suitable plasticizers need to be used depending on the area of application. For example, in the case of polyvinyl chloride compounds used for electric wires and cables, polyvinyl chloride can be used in combination with one or more additives selected from the group consisting of a plasticizer, a filler, a stabilizer, a lubricant, and a flame retardant depending on tensile strength, an elongation rate, plasticization efficiency, volatile loss, tensile strength, an elongation rate, tensile retention, and elongation retention.

Diisodecyl phthalate, which is a plasticizer typically used in the compound industry relating to electric wires and automotive fabrics, is a chemical seen as an endocrine disruptor and its use is being regulated in recent years. Accordingly, there is an increasing demand for the development of an environmentally-friendly plasticizer capable of replacing diisodecyl phthalate. However, until now, the development of an environmentally-friendly plasticizer having a level of physical properties comparable or superior to those of diisodecyl phthalate has not been completely accomplished.

In addition, when polyvinyl chloride is prepared to apply the same in the calendering sheet industry and the like, suitable plasticizers need to be used in consideration of discoloration, migration, processability, and the like. Depending on properties required by industry in various areas of use, such as tensile strength, an elongation rate, light resistance, migration, processability, or the like, a PVC resin is mixed with a plasticizer, a filler, a stabilizer, or the like.

By way of one example, among plasticizer compositions applicable to polyvinyl chloride, the use of di(2-ethylhexyl) terephthalate with a relatively low price results in high viscosity, a relatively low absorption rate of the plasticizer, and low migration. Therefore, it is necessary to continue conducting research on technology for developing a composition that replaces di(2-ethylhexyl) terephthalate and has properties superior to those of di(2-ethylhexyl) terephthalate or a novel composition including di(2-ethylhexyl) terephthalate in order to be optimally applied as a plasticizer for a vinyl chloride-based resin.

DISCLOSURE

Technical Problem

The present invention is directed to providing a plasticizer composition that is environmentally friendly and has high stability.

The present invention is also directed to providing a plasticizer composition that is excellent in basic properties such as plasticization efficiency, migration resistance, hardness, volatile loss, tensile strength, tensile retention, an elongation rate, elongation retention, an absorption rate, stress resistance, cold resistance, and the like.

Technical Solution

One aspect of the present invention provides a plasticizer composition including: a cyclohexane-1,2-diester-based substance of the following Chemical Formula 1; and a citrate-based substance of the following Chemical Formula 2:

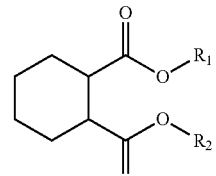

Chemical Formula 1

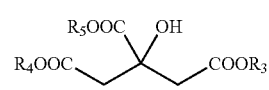

Chemical Formula 2 wherein in Chemical Formula 1 and Chemical Formula 2:
$R_1$ and $R_2$ each independently are a C8 to C10 alkyl group; and
$R_3$ to $R_5$ each independently are a C5 to C10 alkyl group.

Another aspect of the present invention provides a resin composition including: a resin in an amount of 100 parts by weight; and the above-described plasticizer composition in an amount of 5 to 150 parts by weight.

Advantageous Effects

A plasticizer composition according to the present invention is environmentally friendly and has high stability and excellent basic properties.

Therefore, when the plasticizer composition according to the present invention is included in a resin composition, environmental friendliness and excellent properties in terms of plasticization efficiency, migration resistance, hardness, volatile loss, tensile strength, tensile retention, an elongation rate, elongation retention, an absorption rate, stress resistance, and cold resistance can be realized compared with an existing product.

DETAILED DESCRIPTION

Hereinafter, the present invention will be described in more detail to facilitate understanding of the present invention.

Terms and words used in this specification and claims should not be interpreted as being limited to commonly used meanings or meanings in dictionaries, and, based on the principle that the inventors can appropriately define concepts of terms in order to describe their invention in the best way, the terms and words should be interpreted with meanings and concepts which are consistent with the technological spirit of the present invention.

Definition of Terms

As used herein, the term "composition" encompasses a mixture of materials including the composition as well as reaction products and decomposition products formed from materials of the composition.

As used herein, the term "polymer" refers to a polymeric compound prepared by polymerizing homogeneous or heterogeneous monomers. Therefore, the generic term polymer encompasses a homopolymer commonly used to refer to a polymer prepared from only one type of a monomer and an interpolymer as defined below.

As used herein, the term "interpolymer" refers to a polymer prepared by polymerizing at least two types of different monomers. Therefore, the generic term interpolymer encompasses a copolymer commonly used to refer to a polymer prepared from two types of different monomers and a polymer prepared from two or more types of different monomers.

As used herein, the prefix "iso-" is used generically to mean an alkyl group such as a methyl group or an ethyl group is attached as a branched chain to the main chain thereof. In this specification, the prefix "iso-" can be used generically to mean an alkyl group such as a methyl group or an ethyl group is attached as a branched chain to the main chain thereof, including those bonded at the termini of the main chain, unless separately specified otherwise.

In particular, the term "isononyl group" used herein can refer to an alkyl group having a total of 9 carbon atoms in which one or more selected from among one or two methyl groups, one ethyl group, and one propyl group are substituted as a branch to the main chain, and is used generically to mean, for example, a 2-methyloctyl group, a 3-methyloctyl group, a 4-methyloctyl group, a 5-methyloctyl group, a 6-methyloctyl group, a 3-ethylheptyl group, a 2-ethylheptyl group, a 2,5-dimethylheptyl group, a 2,3-dimethylheptyl group, a 4,5-dimethylheptyl group, a 3-ethyl-4-methylhexyl group, a 2-ethyl-4-methylhexyl group, a 2-propylhexyl group, or the like. A commercially available isononyl alcohol (CAS Nos.: 68526-84-1, 27458-94-2) can refer to a composition of isomers having a degree of branching of 1.2 to 1.9, and the commercial alcohol can include a n-nonyl group in some cases.

As used herein, the term "straight vinyl chloride polymer" is one kind of vinyl chloride polymer, can be polymerized through suspension polymerization, bulk polymerization, or the like, and refers to a polymer which is in the form of a porous particle in which a large amount of pores with a size of several tens to several hundreds of micrometers are distributed and has no cohesion and excellent flowability.

As used herein, the term "paste vinyl chloride polymer" is one kind of vinyl chloride polymer, can be polymerized through microsuspension polymerization, microseed polymerization, emulsion polymerization, or the like, and refers to a polymer which is in the form of a fine, compact, and non-porous particle with a size of several tens to several thousands of nanometers and has cohesion and poor flowability.

The terms "comprising", "including", "having", and derivatives thereof are not intended to exclude the presence of any additional components, steps, or procedures, whether they are specifically disclosed or not. To avoid any uncertainty, all compositions claimed through the use of the terms "comprising" and "including", whether polymers or otherwise, can include any additional additives, adjuvants, or compounds unless otherwise stated. In contrast, the term "consisting essentially of" excludes any other component, step, or procedure from the scope of any subsequent description, and excludes those that are not essential to operability. The terms "consisting of" excludes any element, step, or procedure that is not specifically described or listed.

Measurement Methods

In the specification, the contents of components in the composition are analyzed through gas chromatography analysis using a gas chromatography instrument (Agilent 7890 GC manufactured by Agilent Technologies Inc., column: HP-5, carrier gas: helium (flow rate 2.4 mL/min), detector: F.I.D, injection volume: 1 μL, initial value: 70° C./4.2 min, terminal value: 280° C./7.8 min, program rate: 15° C./min).

In the specification, "hardness" refers to Shore hardness (Shore "A" and/or Shore "D") as measured at 25° C. in accordance with ASTM D2240. Hardness is measured using a 3 mm-thick specimen for 10 seconds and can be an index for evaluating plasticization efficiency, and low hardness indicates excellent plasticization efficiency.

In the specification, "tensile strength" is measured in accordance with ASTM D638 as follows. A 1T specimen is pulled at a cross head speed of 200 mm/min using a universal testing machine (UTM; 4466 manufactured by Instron), a time point at which the specimen is broken is then determined, and a load applied at the time point is substituted into the following Equation 1:

$$\text{Tensile strength (kgf/cm}^2\text{)} = \text{Applied load (kgf)/Thickness (cm)} \times \text{Width (cm)} \quad \text{Equation 1}$$

In the specification, "elongation rate" is measured in accordance with ASTM D638 as follows. A 1 mm-thick specimen is pulled at a cross head speed of 200 mm/min using the UTM, a time point at which the specimen is broken is then determined, and a length at the time point is substituted into the following Equation 2:

$$\text{Elongation rate (\%)} = \text{Length after elongation/Initial length} \times 100 \quad \text{Equation 2}$$

In the specification, "migration loss" is measured in accordance with KSM-3156 as follows. A specimen with a thickness of 2 mm or more is prepared, glass plates are attached to both sides of the specimen, and a load of 1 kgf/cm² is then applied. Subsequently, the specimen is placed in a hot-air convection oven (80° C.) for 72 hours, then taken out of the oven, and cooled at room temperature for 4 hours. Afterward, the glass plates attached to both sides of the specimen are removed, weights of the specimen before being placed in and after taken out of the oven along with the glass plate were measured, and the resultant weights are substituted into the following Equation 3:

$$\text{Migration loss (\%)} = \{(\text{Initial weight of specimen at room temperature} - \text{Weight of specimen after being taken out of oven})/\text{Initial weight of specimen at room temperature}\} \times 100 \quad \text{Equation 3}$$

In the specification, "volatile loss" is measured by processing a specimen at 80° C. for 72 hours and then weighing the specimen.

Volatile loss (wt %)={(Initial weight of specimen−Weight of specimen after being processed)/Initial weight of specimen}×100    Equation 4

In the specification, "absorption rate" is evaluated by measuring the time taken to stabilize the torque of a mixer in which a resin and a plasticizer are mixed together using a planetary mixer (Brabender, P600) at 77° C. and 60 rpm.

In the case of the above-described various measurement methods, detailed conditions such as temperature, rotation speed, time, and the like can be slightly varied in some cases, and when the detailed conditions are varied, the measurement method and conditions are separately specified.

1. Plasticizer Composition

A plasticizer composition according to an embodiment of the present invention includes: 1) a cyclohexane-1,2-diester-based substance of the following Chemical Formula 1; and 2) a citrate-based substance of the following Chemical Formula 2:

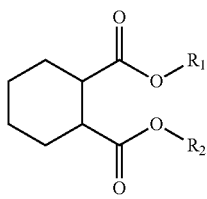

Chemical Formula 1

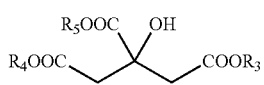

Chemical Formula 2 wherein in Chemical Formula 1 and Chemical Formula 2:
$R_1$ and $R_2$ each independently are a C8 to C10 alkyl group; and
$R_3$ to $R_5$ each independently are a C5 to C10 alkyl group.

The plasticizer composition according to an embodiment of the present invention can further include: 3) a trimellitate-based substance of the following Chemical Formula 3:

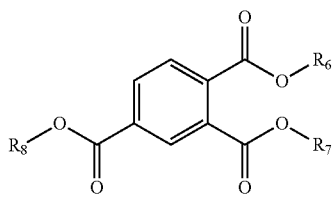

Chemical Formula 3 wherein in Chemical Formula 3:
$R_6$ to $R_8$ each independently are a C4 to C10 alkyl group.

Hereinafter, each component of the plasticizer composition according to an embodiment of the present invention will be described in detail.

1) Cyclohexane-1,2-Diester-Based Substance

The cyclohexane-1,2-diester-based substance has a structure of Chemical Formula 1 and can impart environmental friendliness because phthalate components are not included in the plasticizer composition. In addition, the cyclohexane-1,2-diester-based substance can improve plasticization efficiency, an elongation rate, and migration of the plasticizer composition. Unless ester groups are bound to 1- and 2-positions of carbons of cyclohexane, migration upon compression and migration upon stress are degraded.

The two alkyl groups bonded to ester groups of the cyclohexane-1,2-diester-based substance, $R_1$ and $R_2$, each independently are a C8 to C10 alkyl group. When an alkyl group having less than 8 carbon atoms is used, mechanical properties such as volatile loss, migration loss, tensile strength, and the like are degraded, and an absorption rate or a gelling rate is too high, thereby resulting in adverse effects on processability. On the other hand, when an alkyl group having greater than 10 carbon atoms is used, an absorption rate, processability, and plasticization efficiency can be adversely affected. Therefore, in order to improve these effects, a C8 to C10 alkyl group or a C9 to C10 alkyl group is preferably selected.

$R_1$ and $R_2$ in Chemical Formula 1 can each independently be any one selected from the group consisting of an n-octyl group, an isooctyl group, a 2-ethylhexyl group, an n-nonyl group, an isononyl group, a 2-propylheptyl group, and an isodecyl group, with any one selected from the group consisting of a 2-ethylhexyl group, an isononyl group, a 2-propylheptyl group, and an isodecyl group being preferred and an isononyl group or a 2-propylheptyl group being more preferred.

When the cyclohexane-1,2-diester-based substance of Chemical Formula 1 is directly prepared, direct esterification or trans-esterification of cyclohexane-1,2-dicarboxylic acid or a derivative thereof with an alcohol can be performed.

The derivative of cyclohexane-1,2-dicarboxylic acid can be one or more selected from the group consisting of an anhydride of cyclohexane-1,2-dicarboxylic acid and/or an alkyl ester of cyclohexane-1,2-dicarboxylic acid. Here, the alkyl ester can be a C1 to C12 alkyl ester.

An alkyl group of the finally prepared cyclohexane-1,2-dicarboxyl diester preferably has 8 to 10 carbon atoms or 9 or 10 carbon atoms.

When the cyclohexane-1,2-diester-based substance is prepared by direct esterification, the alcohol can be used in an amount of 2 to 10 moles, 2 to 8 moles, 2 to 6 moles, or 2 to 5 moles with respect to 1 mole of the cyclohexane-1,2-dicarboxylic acid or the derivative thereof, with the range of 2 to 5 moles being preferred.

The direct esterification can be performed in the presence of a catalyst, and the catalyst can be one or more selected from the group consisting of an inorganic acid, an organic acid, and a Lewis acid.

The inorganic acid can be one or more selected from the group consisting of sulfuric acid, hydrochloric acid, and phosphoric acid.

The organic acid can be one or more selected from the group consisting of p-toluenesulfonic acid, methanesulfonic acid, ethanesulfonic acid, propanesulfonic acid, butanesulfonic acid, and alkylsulfuric acid.

The Lewis acid can be one or more selected from the group consisting of aluminum derivatives (aluminum oxide, aluminum hydroxide), tin derivatives (C3 to Cie fatty acid tin, tin oxide, tin hydroxide), titanium derivatives (C3 to C8 tetraalkyl titanate, titanium oxide, titanium hydroxide), lead derivatives (lead oxide, lead hydroxide), and zinc derivatives (zinc oxide, zinc hydroxide).

When the catalyst is a homogeneous catalyst, the catalyst can be used in an amount of 0.01 to 5 parts by weight or 0.01 to 3 parts by weight with respect to 100 parts by weight of the sum of the cyclohexane-1,2-dicarboxylic acid or the derivative thereof and the alcohol, with the range of 0.01 to 3 parts by weight being preferred.

When the catalyst is a heterogeneous catalyst, the catalyst can be used in an amount of 5 to 200 parts by weight or 5 to 100 parts by weight with respect to 100 parts by weight of the sum of the cyclohexane-1,2-dicarboxylic acid or the derivative thereof and the alcohol, with the range of 5 to 200 parts by weight being preferred.

The direct esterification can be performed at 100 to 280° C., 130 to 250° C., or 150 to 230° C., with the range of 150 to 230° C. being preferred.

The direct esterification can be performed for 3 to 30 hours or 3 to 25 hours, with the range of 3 to 25 hours being preferred.

Meanwhile, when the cyclohexane-1,2-diester-based substance of Chemical Formula 1 is prepared by trans-esterification, trans-esterification of a derivative of cyclohexane-1,2-dicarboxylic acid with an alcohol can be performed.

The alcohol can be used in an amount of 2 to 10 moles, 2 to 8 moles, 2 to 6 moles, or 2 to 5 moles with respect to 1 mole of the derivative of cyclohexane-1,2-dicarboxylic acid, with the range of 2 to 5 moles being preferred.

The trans-esterification can be performed in the presence of a catalyst, which provides an effect of reducing a reaction time.

The catalyst can be one or more selected from the group consisting of a Lewis acid and an alkali metal.

Descriptions of the Lewis acid are the same as the description on the direct esterification, and the Lewis acid can be one or more selected from the group consisting of aluminum derivatives (aluminum oxide, aluminum hydroxide), tin derivatives (C3 to C12 fatty acid tin, tin oxide, tin hydroxide), titanium derivatives (C3 to $C_8$ tetraalkyl titanate, titanium oxide, titanium hydroxide), lead derivatives (lead oxide, lead hydroxide), and zinc derivatives (zinc oxide, zinc hydroxide).

The alkali metal can be one or more selected from the group consisting of sodium alkoxide, potassium alkoxide, sodium hydroxide, and potassium hydroxide, and the above-mentioned metallic catalysts can be used alone or in combination with two or more thereof.

The catalyst can be used in an amount of 0.01 to 5 parts by weight or 0.01 to 3 parts by weight with respect to 100 parts by weight of the sum of the derivative of cyclohexane-1,2-dicarboxylic acid and the alcohol, with the range of 0.01 to 3 parts by weight being preferred.

The trans-esterification can be performed at 120 to 250° C., 135 to 230° C., or 140 to 220° C., with the range of 140 to 220° C. being preferred.

The trans-esterification can be performed for 0.5 to 10 hours or 0.5 to 8 hours, with the range of 0.5 to 8 hours being preferred.

In order to promote the discharge of lower alcohol which is produced by the direct esterification or trans-esterification, one or more organic solvents selected from the group consisting of hexane, benzene, toluene, xylene, and cyclohexane, which have a relatively low boiling point, can be further added. In addition, for the same purpose, commercially available nitrogen or the like in an entrained form can be used.

The cyclohexane-1,2-diester-based substance prepared by direct esterification or trans-esterification can be purified by performing separate post-treatment. The post-treatment can be one or more selected from the group consisting of deactivation treatment (neutralization treatment, base treatment) of the catalyst, washing treatment, distillation treatment (decompression or dehydration treatment), and adsorption purification treatment.

Unlike the above-described preparation methods, a preparation method of preparing a cyclohexane-1,2-diester-based substance by hydrogenating a dialkyl phthalate-based substance in the presence of a metallic catalyst can be used.

The hydrogenation is a reaction in which hydrogen is added in the presence of a metallic catalyst to eliminate the aromaticity of a benzene ring of a phthalate and can be a kind of reduction reaction.

The hydrogenation is a reaction in which the phthalate-based substance is reacted with hydrogen in the presence of a metallic catalyst to synthesize a cyclohexane-1,2-diester-based substance, and the hydrogenation conditions can include all the conventional hydrogenation conditions capable of hydrogenating only a benzene ring without affecting a carbonyl group substituted in benzene.

The hydrogenation can be performed by further including an organic solvent such as ethanol or the like, but the present invention is not limited thereto. The metallic catalyst can be a Rh catalyst, a Pt catalyst, a Pd catalyst, or the like, which is commonly used to hydrogenate a benzene ring, but the present invention is not limited thereto as long as it catalyzes a hydrogenation reaction as described above.

2) Citrate-Based Substance

The citrate-based substance has a structure of Chemical Formula 2 and can improve an absorption rate, plasticization efficiency, migration resistance, and the like of the plasticizer composition.

When a citrate-based substance including an acetyl group instead of a hydroxyl group in Chemical Formula 2 is used, degradation of properties (i.e., mechanical properties such as tensile strength and an elongation rate) of a plasticizer composition may not be avoided, and this problem is likely to be exacerbated by low plasticization efficiency. In addition, processes, time, and facility costs for disposal of waste acetic acid generated as a by-product during the preparation of a citrate-based substance including an acetyl group can be additionally required, which leads to an increase in manufacturing costs.

Therefore, a citrate-based substance including an acetyl group instead of a hydroxyl group in Chemical Formula 2 exhibits degraded plasticization efficiency compared to the citrate-based substance of Chemical Formula 2, and an additional amount of the citrate-based substance needs to be increased to overcome the degraded plasticization efficiency, and thus the price of a product can be increased. Therefore, considering various aspects such as marketability, economic feasibility, physical properties, and the like, a citrate-based substance including an acetyl group is not preferred.

$R_3$ to $R_5$ in Chemical Formula 2 each independently are preferably a C5 to C10 alkyl group. When the above-described condition is satisfied, the citrate-based substance has an appropriate molecular weight, and thus plasticization efficiency and an absorption rate of the plasticizer composition can be improved. When $R_3$ to $R_5$ each independently are alkyl groups having less than 5 carbon atoms, tensile strength and volatile loss of the plasticizer composition are degraded, and retention properties are extremely low, thereby resulting in degradation of quality of a final product and a relative increase in an amount of the composition volatilized during processing, which increases the possibility of adverse effects on the atmosphere. In addition, to overcome these problems, excess plasticizer composition needs to be added in an amount as much as the volatilized amount, and thus it is economically disadvantageous. When $R_3$ to $R_5$ each independently are alkyl groups having greater than 10 carbon atoms, the molecular weight of the citrate-based substance is increased, and thus plasticization efficiency and an absorption rate of the plasticizer composition are rather degraded.

In order to improve all of effects on plasticization efficiency, an absorption rate, and migration and effects on tension and tensile retention, elongation and elongation retention, oil resistance, volatile loss, and the like, $R_3$ to $R_5$ are preferably C5 to C10 alkyl groups.

$R_3$ to $R_5$ each independently are any one selected from the group consisting of an n-pentyl group, an isopentyl group, an n-hexyl group, an isohexyl group, an n-heptyl group, an isoheptyl group, an n-octyl group, an isooctyl group, a 2-ethylhexyl group, an n-nonyl group, an isononyl group, a 2-propylheptyl group, and an isodecyl group, with any one selected from the group consisting of a n-pentyl group, an isopentyl group, an n-hexyl group, an isohexyl group, a 2-ethylhexyl group, and an isononyl group being preferred.

Here, specific examples of the isopentyl group include a 2-methylbutyl group, and specific examples of the isohexyl group include a 2-methylpentyl group, a 3-methylpentyl group, a 4-methylpentyl group, a 2,2-dimethylbutyl group, a 2,3-dimethylbutyl group, a 2-ethylbutyl group, and the like.

Two of $R_3$ to $R_5$ can be the same, and the remaining one can be different. In this case, the citrate-based substance of Chemical Formula 2 can be a citrate having combined substituents of two selected from among the above-mentioned substituents, and two substituents can be selected such that a difference in the number of carbon atoms is 1 to 4.

Alternatively, $R_3$ to $R_5$ can be the same. In this case, the citrate-based substance of Chemical Formula 2 can be one or more selected from the group consisting of tri-n-pentyl citrate (TnPC), triisopentyl citrate (TIPC), trihexyl citrate (THxC), triisohexyl citrate (TIHxC), triheptyl citrate (THpC), triisoheptyl citrate (TIHpC), tri(2-ethylhexyl) citrate (TEHC), triisononyl citrate (TINC), and triisodecyl citrate (TIDC).

Specific examples of the triisopentyl citrate include tri(2-methylbutyl) citrate and the like, and specific examples of the triisohexyl citrate include tri(2-methylpentyl) citrate, tri(3-methylpentyl) citrate, tri(4-methylpentyl) citrate, tri(2,2-dimethylbutyl) citrate, tri(2,3-dimethylbutyl) citrate, tri(2-ethylbutyl) citrate, and the like.

Meanwhile, the weight ratio of the cyclohexane-1,2-diester-based substance of Chemical Formula 1 and the citrate-based substance of Chemical Formula 2 can be 95:5 to 5:95, 90:10 to 10:90, or 80:20 to 20:80, with the range of 80:20 to 20:80 being preferred. When the above-described content is satisfied, quality such as plasticization efficiency, an absorption rate, migration resistance, and the like can be improved.

When the citrate-based substance of Chemical Formula 2 is directly prepared, direct esterification or trans-esterification of citric acid or a derivative thereof with an alcohol can be performed.

The derivative of citric acid can be one or more selected from the group consisting of an anhydride of citric acid and an alkyl ester of citric acid. The alkyl ester can be a C1 to C6 alkyl ester, and the alcohol is preferably a C5 to C10 alcohol.

When the citrate-based substance of Chemical Formula 2 is prepared by direct esterification or trans-esterification, the alcohol can be used in an amount of 3 to 15 moles, 3 to 12 moles, or 3 to 10 moles with respect to 1 mole of the citric acid or the derivative thereof, with the range of 3 to 10 moles being preferred.

Additional descriptions of direct esterification and trans-esterification are the same as the descriptions in the preparation method of the cyclohexane-1,2-diester-based substance of Chemical Formula 1.

3) Trimellitate-Based Substance

The trimellitate-based substance has a structure of Chemical Formula 3 and can impart environmental friendliness and high stability to the plasticizer composition. In addition, the trimellitate-based substance can improve properties, such as migration resistance, volatile loss, tensile retention, oil resistance, and the like, of the plasticizer composition. In particular, the plasticizer composition to which the trimellitate-based substance is applied is favorable in the compound industry.

$R_6$ to $R_8$ in Chemical Formula 3 can each independently be a C4 to C10 alkyl group, a C5 to C10 alkyl group, a C5 to C9 alkyl group, or a C6 to C9 alkyl group, with the C6 to C9 alkyl group being preferred. When the above-described condition is satisfied, migration resistance, volatile loss, elongation retention, oil resistance, and migration upon stress can be improved.

$R_6$ to $R_8$ can each independently be any one selected from the group consisting of an n-butyl group, an isobutyl group, an n-pentyl group, an isopentyl group, an n-hexyl group, an n-heptyl group, an isoheptyl group, an n-octyl group, an isooctyl group, a 2-ethylhexyl group, an n-nonyl group, an isononyl group, a 2-propylheptyl group, and an isodecyl group, with a 2-ethylhexyl group or an isononyl group being preferred.

In this case, when the alkyl group is linear, cold resistance can be improved, and when the alkyl group is branched, economic feasibility can be improved.

The trimellitate-based substance of Chemical Formula 3 can be included in an amount of 1 to 150 parts by weight, 5 to 125 parts by weight, 10 to 100 parts by weight, or 20 to 100 parts by weight with respect to 100 parts by weight of the sum of the cyclohexane-1,2-diester-based substance of Chemical Formula 1 and the citrate-based substance of Chemical Formula 2, with the range of 20 to 100 parts by weight being preferred. When the above-described range is satisfied, quality such as oil resistance, tensile and elongation retention, volatile loss, and the like can be improved.

When the trimellitate-based substance of Chemical Formula 3 is directly prepared, direct esterification or trans-esterification of trimellitic acid or a derivative thereof with an alcohol can be performed.

The derivative of trimellitic acid can be one or more selected from the group consisting of an anhydride of trimellitic acid and an alkyl ester of trimellitic acid. Here, the alkyl ester can be a C1 to C6 alkyl ester.

The alcohol is a C4 to C10 alcohol, and can be a C5 to C10 alcohol, a C5 to C9 alcohol, or a C6 to C9 alcohol, with the C6 to C9 alcohol being preferred.

When the trimellitate-based substance of Chemical Formula 3 is prepared by direct esterification, the alcohol can be used in an amount of 3 to 15 moles, 3 to 12 moles, or 3 to 10 moles with respect to 1 mole of the trimellitic acid or the derivative thereof, with the range of 3 to 10 moles being preferred.

Additional descriptions of direct esterification are the same as the descriptions in the preparation method of the cyclohexane-1,2-diester-based sub stance.

Meanwhile, when the trimellitate-based substance of Chemical Formula 3 is prepared by trans-esterification, trans-esterification of a derivative of trimellitic acid with an alcohol can be performed. In this case, the derivative of trimellitic acid can be an alkyl ester of trimellitic acid.

The alcohol can be used in an amount of 3 to 15 moles, 3 to 12 moles, or 3 to 10 moles with respect to 1 mole of the derivative of trimellitic acid, with the range of 3 to 10 moles being preferred.

Additional descriptions of trans-esterification are the same as the descriptions in the preparation method of the cyclohexane-1,2-diester-based substance of Chemical Formula 1.

2. Resin Composition

A resin composition according to another embodiment of the present invention includes: a resin in an amount of 100 parts by weight; and the plasticizer composition according to an embodiment of the present invention in an amount of 5 to 150 parts by weight.

The resin can be any resin known in the art. For example, a mixture of one or more selected from the group consisting of a straight vinyl chloride polymer, a paste vinyl chloride polymer, an ethylene-vinyl acetate copolymer, an ethylene polymer, a propylene polymer, polyketone, polystyrene, polyurethane, natural rubber, synthetic rubber, and a thermoplastic elastomer can be used, but the present invention is not limited thereto.

The plasticizer composition can be included in an amount of 5 to 150 parts by weight, preferably, 5 to 130 parts by weight or 10 to 120 parts by weight with respect to 100 parts by weight of the resin.

In general, a resin in which a plasticizer composition is used can be subjected to melt processing or plastisol processing to prepare a resin product, and the resin for melt processing and the resin for plastisol processing can be produced differently according to a polymerization method.

For example, when used in melt processing, a vinyl chloride polymer is prepared through suspension polymerization or the like and thus used as a solid-phase resin particle having a large average particle diameter. In this case, the vinyl chloride polymer is called a straight vinyl chloride polymer. When used in plastisol processing, a vinyl chloride polymer is prepared through emulsion polymerization or the like and thus used as a fine sol-phase resin particles. In this case, the vinyl chloride polymer is called a paste vinyl chloride polymer.

In the case of the straight vinyl chloride polymer, the plasticizer composition is preferably included in an amount of 5 to 80 parts by weight with respect to 100 parts by weight of the polymer, and in the case of the paste vinyl chloride polymer, the plasticizer composition is preferably included in an amount of 40 to 120 parts by weight with respect to 100 parts by weight of the polymer.

The resin composition can further include a filler. The filler can be included in an amount of 0 to 300 parts by weight, preferably 50 to 200 parts by weight, and more preferably 100 to 200 parts by weight with respect to 100 parts by weight of the resin.

The filler can be any filler known in the art without particular limitation. For example, a mixture of one or more selected from silica, magnesium carbonate, calcium carbonate, hard charcoal, talc, magnesium hydroxide, titanium dioxide, magnesium oxide, calcium hydroxide, aluminum hydroxide, aluminum silicate, magnesium silicate, and barium sulfate can be used.

In addition, the resin composition can further include other additives such as a stabilizer and the like as necessary. The additives such as a stabilizer and the like can be included, for example, in an amount of 0 to 20 parts by weight, preferably 1 to 15 parts by weight with respect to 100 parts by weight of the resin.

Examples of the stabilizer include a calcium-zinc (Ca—Zn)-based stabilizer such as a complex stearate of calcium and zinc and the like and a barium-zinc (Ba—Zn)-based stabilizer, but the present invention is not particularly limited thereto.

The resin composition can be applied to both melt processing and plastisol processing as described above, wherein the melt processing can be, for example, calendering processing, extrusion processing, or injection processing, and the plastisol processing can be coating processing or the like.

Hereinafter, the present invention will be described in detail with reference to embodiments so that those skilled in the art can easily carry out the present invention. However, the present invention can be embodied in several different forms, and therefore, is not limited to embodiments described herein.

Preparation Example 1: Diisononyl cyclohexane-1,2-diester 516.5 g of cyclohexane-1,2-dicarboxylic acid, 1,296 g of isononyl alcohol, and 1.55 g of tetraisopropyl titanate as a catalyst were put into a 3 L four-neck reaction vessel equipped with a cooler, a condenser, a decanter, a reflux pump, a temperature controller, a stirrer, and the like, and the temperature of the reaction vessel was set at 230° C. Then, direct esterification was performed for about 6 hours while continuously introducing nitrogen gas and terminated when an acid value reached 0.1.

After the reaction was completed, distillation extraction was performed under reduced pressure to remove unreacted raw materials. Afterward, neutralization, dehydration, and filtration processes were performed to prepare 1,240 g of diisononyl cyclohexane-1,2-dicarboxylate (DINCH) (yield: 97%).

Preparation Example 2: Di(2-propylheptyl) cyclohexane-1,2-diester 1,320 g (yield: 97%) of di(2-propylheptyl) cyclohexane-1,2-dicarboxylate (DPHpCH) was obtained in the same manner as in Preparation Example 1 except that 516.5 g of cyclohexane-1,2-dicarboxylic acid and 1,422 g of 2-propylheptanol were put into a reaction vessel.

Preparation Example 3: Tri(n-butyl) citrate 700 g (yield: 97%) of tri(n-butyl) citrate (TnBC) was obtained in the same manner as in Preparation Example 1 except that 384.2 g of an anhydride of citric acid and 670 g of n-butanol were put into a reaction vessel.

Preparation Example 4: Tri(n-pentyl) citrate 780 g (yield: 97%) of tri(n-pentyl) citrate (TnPC) was obtained in the same manner as in Preparation Example 1 except that 384.2 g of an anhydride of citric acid and 794 g of n-pentanol were put into a reaction vessel.

Preparation Example 5: Tri(n-hexyl) citrate 863 g (yield: 97%) of tri(n-hexyl) citrate (TnHxC) was obtained in the same manner as in Preparation Example 1 except that 384.2 g of an anhydride of citric acid and 918 g of n-hexanol were put into a reaction vessel.

Preparation Example 6: Tri(2-ethylhexyl) citrate 1,026 g (yield: 97%) of tri(2-ethylhexyl) citrate (TEHC) was obtained in the same manner as in Preparation Example 1 except that 384.2 g of an anhydride of citric acid and 1,170 g of 2-ethylhexanol were put into a reaction vessel.

Preparation Example 7: Triisononyl citrate 1,108 g (yield: 97%) of triisononyl citrate (TINC) was obtained in the same manner as in Preparation Example 1 except that 384.2 g of an anhydride of citric acid and 1,296 g of isononanol were put into a reaction vessel.

Preparation Example 8: Tri(2-ethylhexyl) trimellitate 1,060 g (yield: 97%) of tri(2-ethylhexyl) trimellitate (TEHTM) was obtained in the same manner as in Preparation Example 1 except that 384 g of anhydrous trimellitic acid and 1,170 g of 2-ethylhexanol were put into a reaction vessel.

Preparation Example 9: Triisononyl trimellitate 1,140 g (yield: 97%) of triisononyl trimellitate (TINTM) was obtained in the same manner as in Preparation Example 1 except that 384 g of anhydrous trimellitic acid and 1,296 g of isononanol were put into a reaction vessel.

One or more of the substances prepared in Preparation Examples 1 to 9 were mixed to prepare plasticizer compositions of Example and Comparative Examples, and these are summarized in the following [Table 1] to [Table 5]. Physical properties of the plasticizer compositions were evaluated according to the following test items. Commercially available products were used as substances other than the substances prepared in Preparation Examples.

<Test Items>

Measurement of Hardness (Shore "A" and Shore "D")

In accordance with ASTM D2240, the hardness of a 3 mm-thick specimen was measured for 10 seconds.

Measurement of Tensile Strength (Kgf/Cm$^2$)

In accordance with ASTM D638, a 1 mm-thick specimen was pulled at a cross head speed of 200 mm/min using a universal testing machine (UTM; 4466 manufactured by Instron), and a time point at which the specimen was broken was then determined.

Measurement of Elongation Rate (%)

In accordance with ASTM D638, a 1 mm-thick specimen was pulled at a cross head speed of 200 mm/min using a universal testing machine (UTM; 4466 manufactured by Instron), and a time point at which the specimen was broken was then determined. Afterward, a length at the time point was substituted into the following Equation 1 to obtain an elongation rate.

Elongation rate (%): [(Length at the time point when specimen was broken)/(Initial length)]×100    <Equation 1>

Measurement of Tensile and Elongation Retention (%)

In the measurement of tensile and elongation retention, a specimen was heated at 113° C. for 168 hours, and tensile strength remaining in the specimen and an elongation rate were then measured. Measurement methods are the same as the above-described measurement methods of tensile strength and an elongation rate.

Measurement of Migration Loss (%)

In accordance with KSM-3156, PS plates were attached to both sides of a 1 mm-thick specimen, and a load of 1 or 2 kgf/cm$^2$ was then applied thereto. The specimen was placed in a hot-air convection oven (80° C.) for 72 hours, then taken out of the oven, and cooled at room temperature. Afterward, the PS plates attached to both sides of the specimen were removed, weights of the specimen before being placed in and after taken out of the oven were measured, and the resultant weights were substituted into the following Equation 2 to obtain a migration loss value.

Migration loss (%)=[(Initial weight of specimen before test)−(Weight of specimen after test)]/(Initial weight of specimen before test)×100    <Equation 2>

Measurement of Volatile Loss (%)

A 1 mm-thick specimen was exposed to 80° C. for 72 hours or at 113° C. for 168 hours, a weight thereof was then measured, and the resultant weight was substituted into the following Equation 3 to obtain a volatile loss value.

Volatile loss (%)=[(Initial weight of specimen)−(Weight of specimen after being exposed)]/(Initial weight of specimen)×100    <Equation 3>

Migration Upon Stress

A 2 mm-thick specimen in a bent state was left to stand at 23° C. for 168 hours, and a degree of migration (leaking degree) was then observed and expressed as a numerical value. In this case, values closer to 0 indicate good characteristics.

0: very good, 1: good, 2: fair, 3: poor

Evaluation of Absorption Rate

An absorption rate was evaluated by measuring the time taken to stabilize the torque of a mixer in which a resin composition and an ester compound are mixed together using a planetary mixer (P600 manufactured by Brabender) at 77° C. and 60 rpm.

1: very good, 2: good, 3: fair, 4: poor, 5: very poor

Oil Resistance

A 1 mm-thick specimen was left to stand in IRM-902 oil at 70° C. for 4 hours, and tensile strength remaining in the specimen and an elongation rate were then measured. Measurement methods are the same as the above-described measurement methods of tensile strength and an elongation rate.

Experimental Example 1: Evaluation of Physical Properties for Calendering Application Specimens were prepared using plasticizer compositions of Examples and Comparative Examples described in the following [Table 1] and [Table 2].

For specimen preparation, in accordance with ASTM D638, 100 parts by weight of polyvinyl chloride (LS100 manufactured by LG Chem Ltd.), 40 parts by weight of each of the plasticizer compositions prepared in Examples and Comparative Examples, and 3 parts by weight of a stabilizer (RUP-144 manufactured by ADEKA CORPORATION) were mixed while stirring at 98° C. and 700 rpm, and the resultant mixture was subjected to roll-milling at 160° C. for 4 minutes and pressed using a press at 180° C. for 3 minutes (low pressure) and for 2.5 minutes (high pressure), thereby preparing 1 mm-thick and 3 mm-thick specimens.

Each of the specimens was subjected to tests for evaluating the above-described physical properties, and results thereof are shown in the following [Table 1] and [Table 2]. Migration loss was measured after a load of 1 kgf/cm$^2$ was applied, and volatile loss was measured after each specimen was exposed to 80° C. for 72 hours.

TABLE 1

| Classification | | | Examples | | | | |
| --- | --- | --- | --- | --- | --- | --- | --- |
| | | | 1 | 2 | 3 | 4 | 5 |
| Plasticizer composition (parts by weight) | Cyclohexane-1,2-diester-based substance | DINCH | 70 | 30 | 70 | 30 | — |
| | | DPHpCH | — | — | — | — | 50 |
| | Citrate-based substance | TnPC | 30 | 70 | — | — | 50 |
| | | TnHxC | — | — | 30 | 70 | — |
| Shore A hardness | | | 91.9 | 89.8 | 87.7 | 89.8 | 90.6 |
| Tensile strength | | | 242.9 | 239.6 | 230.6 | 240.6 | 233.7 |
| Elongation rate | | | 337.1 | 334.1 | 337.8 | 347.8 | 335.3 |
| Migration loss | | | 3.79 | 3.07 | 2.52 | 2.12 | 3.05 |
| Volatile loss | | | 1.20 | 1.46 | 1.85 | 1.30 | 0.88 |
| Migration upon stress | | | 1.0 | 0 | 0 | 0 | 0 |
| Absorption rate | | | 3 | 1 | 1 | 1 | 2 |

TABLE 2

| Classification | | | Comparative Examples | | | | | |
| --- | --- | --- | --- | --- | --- | --- | --- | --- |
| | | | 1 | 2 | 3 | 4 | 5 | 6 |
| Plasticizer composition (parts by weight) | Cyclohexane-1,2-diester-based substance | DINCH | — | 100 | — | 50 | 70 | 50 |
| | Citrate-based substance | TnBC | — | — | — | 50 | — | — |
| | | TEHC | — | — | 100 | — | — | — |
| | | ATBC | — | — | — | — | 30 | — |
| | | ATEHC | — | — | — | — | — | 50 |
| Diisodecyl phthalate | | | 100 | — | — | — | — | — |
| Shore A hardness | | | 94.4 | 94.3 | 98.8 | 88.4 | 90.8 | 97.2 |
| Tensile strength | | | 235.0 | 225.0 | 247.6 | 207.3 | 241.9 | 245.6 |
| Elongation rate | | | 286.3 | 306.7 | 274.2 | 312.0 | 306.7 | 274.0 |
| Migration loss | | | 2.30 | 5.10 | 4.32 | 2.84 | 3.80 | 5.32 |
| Volatile loss | | | 1.64 | 1.07 | 0.68 | 6.74 | 1.25 | 1.41 |
| Migration upon stress | | | 1.0 | 2.0 | 3.0 | 1.0 | 0.5 | 3 |
| Absorption rate | | | 4 | 5 | 5 | 1 | 3 | 5 |

ATBC: Acetyl tributyl citrate
TEHC: Acetyl tri(2-ethylhexyl) citrate

Referring to Table 1 and Table 2, it can be seen that Examples 1 to 5 exhibited superior levels of plasticization efficiency, an elongation rate, an absorption rate and equivalent levels of tensile strength and volatile loss to Comparative Example 1, that is, diisodecyl phthalate, whereas volatile loss was slightly degraded. From these results, it can be seen that since the plasticizer compositions according to an embodiment of the present invention realize physical properties superior or comparable to those of diisodecyl phthalate which is an existing plasticizer and are environmentally friendly, they can replace diisodecyl phthalate.

On the other hand, it can be seen that Comparative Example 2 not including the citrate-based substance exhibited degraded properties in terms of plasticization efficiency, tensile strength, an elongation rate, migration loss, migration upon stress, and an absorption rate compared to Examples. It can be seen that Comparative Example 3 not including the cyclohexane-1,2-diester-based substance exhibited degraded properties in terms of plasticization efficiency, an elongation rate, migration loss, migration upon stress, and an absorption rate compared to Examples. It can be seen that Comparative Example 4 including tri(n-butyl) citrate exhibited degraded properties in terms of tensile strength, an elongation rate, and volatile loss compared to Examples.

It can be seen that Comparative Example 5 including acetyl tributyl citrate exhibited a low elongation rate compared to Examples. It can be seen that Comparative Example 6 including acetyl tri(2-ethylhexyl) citrate exhibited degraded properties in terms of plasticization efficiency, an elongation rate, migration loss, and an absorption rate compared to Examples. In addition, since a citrate-based substance including an acetyl group additionally required an acetylation process during the preparation thereof, not only costs increase, but also cost competitiveness can decrease due to generation and disposal of by-products.

Experimental Example 2: Evaluation of Physical Properties of Compound

Specimens were prepared using plasticizer compositions of Examples and Comparative Examples described in the following Table 3 to Table 5.

For specimen preparation, in accordance with ASTM D638, 100 parts by weight of polyvinyl chloride (LS100 manufactured by LG Chem Ltd.), 50 parts by weight of each of the plasticizer compositions prepared in Examples and Comparative Examples, 40 parts by weight of a filler (Omyacrab® 1T manufactured by Omya Inc.), 5 parts by weight of a stabilizer (RUP-144 manufactured by ADEKA CORPORATION), and 0.3 part by weight of a lubricant (ST-A manufactured by ISU CHEMICAL) were mixed while stirring at 98° C. and 700 rpm, and the resultant mixture was subjected to roll-milling at 160° C. for 4 minutes and pressed using a press at 180° C. for 3 minutes (low pressure) and for 2.5 minutes (high pressure), thereby preparing 1 mm-thick and 3 mm-thick specimens.

Each of the specimens was subjected to tests for evaluating the above-described physical properties, and results thereof are shown in the following Table 3 to Table 5.

TABLE 3

| Classification | | | Examples 6 | 7 | 8 | 9 |
|---|---|---|---|---|---|---|
| Plasticizer composition (parts by weight) | Cyclohexane-1,2-diester-based substance | DINCH | 50 | 30 | 40 | 10 |
| | Citrate-based substance | TEHC | 50 | 70 | — | — |
| | | TINC | — | — | 60 | 90 |
| Hardness | | A | 92.8 | 92.7 | 94.6 | 95.1 |
| | | D | 45.5 | 45.4 | 47.9 | 48.8 |

TABLE 3-continued

| Classification | | Examples 6 | 7 | 8 | 9 |
|---|---|---|---|---|---|
| Tensile strength | | 177.2 | 174.3 | 179.0 | 178.3 |
| Tensile retention | | 100.3 | 98.7 | 98.7 | 99.6 |
| Elongation rate | | 268.4 | 280.0 | 272.5 | 275.5 |
| Elongation retention | | 85.9 | 88.6 | 81.7 | 82.1 |
| Oil resistance | Tensile retention | 97.7 | 95.9 | 85.7 | 85.9 |
| | Elongation retention | 85.4 | 87.8 | 72.1 | 70.9 |
| Migration loss | | 1.86 | 1.56 | 1.82 | 0.95 |
| Volatile loss | | 4.56 | 3.94 | 3.20 | 3.00 |

TABLE 4

| Classification | | | Examples 10 | 11 | 12 | 13 | 14 |
|---|---|---|---|---|---|---|---|
| Plasticizer composition (parts by weight) | Cyclohexane-1,2-diester-based substance | DINCH | 40 | 30 | 50 | 30 | 40 |
| | Citrate-based substance | TEHC | 30 | 20 | — | — | — |
| | | TINC | — | — | 30 | 30 | 50 |
| | Trimellitate-based substance | TEHTM | 30 | 50 | 20 | 40 | 10 |
| | | TINTM | — | — | 20 | 40 | 10 |
| Hardness | | A | 92.9 | 93.4 | 94.3 | 95.1 | 94.5 |
| | | D | 46.4 | 47.0 | 48.3 | 48.9 | 48.3 |
| Tensile strength | | | 171.1 | 178.6 | 174.7 | 187.6 | 172.3 |
| Tensile retention | | | 101.0 | 100.8 | 100.5 | 99.4 | 98.4 |
| Elongation rate | | | 281.4 | 294.3 | 280.9 | 295.8 | 281.6 |
| Elongation retention | | | 87.0 | 93.5 | 89.4 | 95.6 | 92.4 |
| Oil resistance | Tensile retention | | 89.9 | 92.4 | 86.6 | 93.4 | 92.0 |
| | Elongation retention | | 79.8 | 86.7 | 78.6 | 88.2 | 85.4 |
| Migration loss | | | 1.32 | 0.86 | 1.41 | 0.90 | 1.02 |
| Volatile loss | | | 4.31 | 3.25 | 4.86 | 2.45 | 3.14 |

TABLE 5

| Classification | | | Comparative Examples 7 | 8 | 9 | 10 | 11 | 12 |
|---|---|---|---|---|---|---|---|---|
| Plasticizer composition | Cyclohexane-1,2-diester-based substance | DINCH | — | 100 | — | 50 | 70 | 50 |
| | Citrate-based substance | TnBC | — | — | — | 50 | — | — |
| | | TEHC | — | — | 100 | — | — | — |
| | | ATBC | — | — | — | — | 30 | — |
| | | ATEHC | — | — | — | — | — | 50 |
| | Diisodecyl phthalate (parts by weight) | | 100 | — | — | — | — | — |
| Hardness | | A | 93.4 | 92.3 | 99.4 | 89.0 | 91.4 | 97.8 |
| | | D | 46.8 | 45.1 | 52.3 | 43.8 | 51.0 | |
| Tensile strength | | | 161.3 | 154.0 | 170.2 | 150.3 | 148.3 | 159.7 |
| Tensile retention | | | 104.5 | 74.8 | 100.1 | 57.6 | 61.0 | 82.4 |
| Elongation rate | | | 267.6 | 270.1 | 245.7 | 250.8 | 235.9 | 260.3 |
| Elongation retention | | | 86.4 | 58.6 | 74.2 | 43.0 | 44.2 | 60.2 |
| Oil resistance | Tensile retention | | 86.2 | 62.0 | 82.3 | 40.8 | 48.7 | 75.0 |
| | Elongation retention | | 72.5 | 52.8 | 60.2 | 35.1 | 45.6 | 69.4 |
| Migration loss | | | 2.04 | 2.58 | 4.58 | 5.30 | 6.02 | 3.88 |
| Volatile loss | | | 4.85 | 5.06 | 1.24 | 15.9 | 8.66 | 4.20 |

ATBC: Acetyl tributyl citrate
TEHC: Acetyl tri(2-ethylhexyl) citrate

Referring to Table 3 to Table 5, it can be seen that Examples 6 to 14 exhibited equivalent levels of plasticization efficiency, tensile retention, elongation retention, and oil resistance and superior levels of tensile strength, an elongation rate, migration loss, and volatile loss to Comparative Example 7, that is, diisodecyl phthalate. From these results, it can be seen that since the plasticizer compositions according to an embodiment of the present invention realize physical properties superior or comparable to those of diisodecyl phthalate which is an existing plasticizer and are environmentally friendly, they can replace diisodecyl phthalate.

On the other hand, it can be seen that Comparative Example 8 not including the citrate-based substance exhibited degraded properties in terms of tensile strength, an elongation rate, and migration loss compared to Examples. It can be seen that Comparative Example 9 not including the cyclohexane-1,2-diester-based substance exhibited degraded properties in terms of plasticization efficiency, tensile strength, an elongation rate, elongation retention, oil resistance, and migration loss compared to Examples. It can be seen that Comparative Example 10 including tri(n-butyl) citrate exhibited degraded properties in terms of tensile strength, an elongation rate, elongation retention, oil resistance, migration loss, and volatile loss compared to Examples.

It can be seen that Comparative Example 11 including acetyl tributyl citrate exhibited degraded properties in terms of tensile strength, tensile retention, an elongation rate, elongation retention, oil resistance, migration loss, and volatile loss compared to Examples. It can be seen that Comparative Example 12 including acetyl tri(2-ethylhexyl) citrate exhibited degraded properties in terms of plasticization efficiency, tensile strength, tensile retention, an elongation rate, elongation retention, oil resistance, and migration loss compared to Examples. In addition, since a citrate-based substance including an acetyl group additionally required an acetylation process during the preparation thereof, not only costs increase, but also cost competitiveness can decrease due to generation and disposal of by-products.

The invention claimed is:

1. A plasticizer composition comprising:
   a cyclohexane-1,2-diester-based substance of the following Chemical Formula 1; and
   a citrate-based substance of the following Chemical Formula 2,
   wherein a weight ratio of the cyclohexane-1,2-diester-based substance of Chemical Formula 1 and the citrate-based substance of Chemical Formula 2 is 70:30 to 5:95:

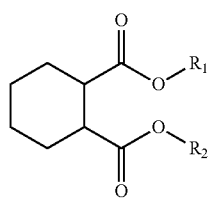

Chemical Formula 1

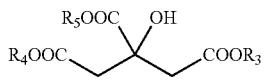

Chemical Formula 2 wherein in Chemical Formula 1 and Chemical Formula 2:
$R_1$ and $R_2$ each independently are a C8 to C10 alkyl group; and
$R_3$ to $R_5$ each independently are a C5 to C10 alkyl group.

2. The plasticizer composition of claim 1, wherein the $R_1$ and $R_2$ each independently are a C9 or C10 alkyl group.

3. The plasticizer composition of claim 1, wherein the $R_1$ and $R_2$ each independently are any one selected from the group consisting of a n-octyl group, an isooctyl group, a 2-ethylhexyl group, an n-nonyl group, an isononyl group, a 2-propylheptyl group, and an isodecyl group.

4. The plasticizer composition of claim 1, wherein the $R_3$ to $R_5$ each independently are any one selected from the group consisting of a n-pentyl group, an isopentyl group, an n-hexyl group, an isohexyl group, an n-heptyl group, an isoheptyl group, an n-octyl group, an isooctyl group, a 2-ethylhexyl group, a n-nonyl group, an isononyl group, a 2-propylheptyl group, and an isodecyl group.

5. The plasticizer composition of claim 1, further comprising a trimellitate-based substance of the following Chemical Formula 3:

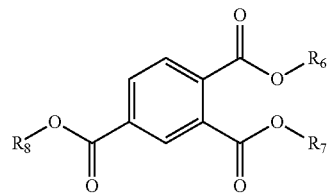

Chemical Formula 3 wherein $R_6$ to $R_8$ each independently are a C4 to C10 alkyl group.

6. The plasticizer composition of claim 5, wherein the $R_6$ to $R_8$ each independently are a C5 to C10 alkyl group.

7. The plasticizer composition of claim 5, wherein the $R_6$ to $R_8$ each independently are any one selected from the group consisting of an n-butyl group, an isobutyl group, an n-pentyl group, an isopentyl group, an n-hexyl group, an isohexyl group, a n-heptyl group, an isoheptyl group, an n-octyl group, an isooctyl group, a 2-ethylhexyl group, an n-nonyl group, an isononyl group, a 2-propylheptyl group, and an isodecyl group.

8. The plasticizer composition of claim 5, wherein the trimellitate-based substance of Chemical Formula 3 is present in an amount of 1 to 150 parts by weight with respect to 100 parts by weight of the sum of the cyclohexane-1,2-diester-based substance of Chemical Formula 1 and the citrate-based substance of Chemical Formula 2.

9. A resin composition comprising:
   a resin in an amount of 100 parts by weight; and
   the plasticizer composition of claim 1 in an amount of 5 to 150 parts by weight.

10. The resin composition of claim 9, wherein the resin is one or more selected from the group consisting of a straight vinyl chloride polymer, a paste vinyl chloride polymer, an ethylene-vinyl acetate copolymer, an ethylene polymer, a propylene polymer, polyketone, polystyrene, polyurethane, natural rubber, synthetic rubber, and a thermoplastic elastomer.

* * * * *